US012755839B2

(12) United States Patent
Comito et al.

(10) Patent No.: US 12,755,839 B2
(45) Date of Patent: Oct. 6, 2026

(54) MACHINE LEARNING MODEL BASED CONDITION AND PROPERTY DETECTION

(71) Applicant: Disney Enterprises, Inc., Burbank, CA (US)

(72) Inventors: Keith Comito, Seaford, NY (US); Gregory Brooks Hale, Orlando, FL (US); Komath Naveen Kumar, Los Angeles, CA (US)

(73) Assignee: Disney Enterprises, Inc., Burbank, CA (US)

( * ) Notice: Subject to any disclaimer, the term of this patent is extended or adjusted under 35 U.S.C. 154(b) by 228 days.

(21) Appl. No.: 17/752,741

(22) Filed: May 24, 2022

(65) Prior Publication Data

US 2022/0384040 A1 Dec. 1, 2022

Related U.S. Application Data

(60) Provisional application No. 63/194,018, filed on May 27, 2021.

(51) Int. Cl.
*G16H 50/20* (2018.01)
*G06N 20/20* (2019.01)

(52) U.S. Cl.
CPC ............. *G16H 50/20* (2018.01); *G06N 20/20* (2019.01)

(58) Field of Classification Search
CPC ........ G10L 25/66; G16H 50/02; G16H 50/70; G16H 50/20; G06N 3/098; A61B 5/4803
See application file for complete search history.

(56) References Cited

U.S. PATENT DOCUMENTS 10,475,468 B1 * 11/2019 Yelchuru .................. F24F 11/30
2015/0073306 A1 * 3/2015 Abeyratne ............. G16H 50/30
600/586

(Continued)

FOREIGN PATENT DOCUMENTS

WO WO 2018/141013 A2 8/2018
WO WO 2021/119742 A1 6/2021

(Continued)

OTHER PUBLICATIONS

Lella et al.; Automatic COVID-19 disease diagnosis using 1D convolutional neural network and augmentation with human respiratory sound based on parameters: cough, breath, and voice; Mar. 10, 2021; AIMS Public Health; 8(2) (Year: 2021).*

(Continued)

*Primary Examiner* — Karen A Hranek
(74) *Attorney, Agent, or Firm* — Farjami & Farjami LLP

(57) ABSTRACT

A system for performing machine language (ML) model based condition and property detection includes a computing platform having processing hardware and a system memory storing a software code that includes a trained ML model. The processing hardware is configured to execute the software code to receive a dataset, and perform an analysis of the dataset, using a first stage of the trained ML model, to detect a presence of a predetermined data attribute. The processing hardware is further configured to execute the software code to predict, using a second stage of the trained ML model when the analysis of the dataset detects the presence of the predetermined data attribute, a probability that the predetermined data attribute is indicative of a condition or a property.

12 Claims, 10 Drawing Sheets

(56) References Cited

U.S. PATENT DOCUMENTS

| | | | | |
|---|---|---|---|---|
| 2015/0351663 | A1* | 12/2015 | Zigel | G10L 25/66 600/586 |
| 2017/0304732 | A1* | 10/2017 | Velic | G06V 10/774 |
| 2018/0260612 | A1* | 9/2018 | Richards | G06N 5/046 |
| 2019/0042911 | A1* | 2/2019 | Koren | G06N 3/04 |
| 2019/0088367 | A1* | 3/2019 | Stamatopoulos | G16H 50/20 |
| 2019/0385711 | A1* | 12/2019 | Shriberg | A61B 5/164 |
| 2020/0015709 | A1 | 1/2020 | Peltonen | |
| 2020/0293887 | A1* | 9/2020 | De Brouwer | G06N 3/084 |
| 2021/0076977 | A1* | 3/2021 | Abeyratne | A61B 5/113 |
| 2021/0125732 | A1* | 4/2021 | Patel | G06N 5/01 |
| 2021/0361227 | A1* | 11/2021 | Chou | A61B 5/0022 |
| 2022/0061694 | A1* | 3/2022 | Ayu | A61B 5/7267 |
| 2022/0110542 | A1* | 4/2022 | Thomas | A61B 5/4803 |
| 2022/0180890 | A1* | 6/2022 | Ramaiah | G06N 20/00 |
| 2022/0206483 | A1* | 6/2022 | Bhat | G05B 23/0237 |
| 2023/0015028 | A1* | 1/2023 | Peltonen | G16H 50/20 |
| 2023/0045078 | A1* | 2/2023 | Berisha | A61B 5/486 |
| 2023/0190140 | A1* | 6/2023 | Tiron | A61B 5/746 600/534 |
| 2023/0329630 | A1* | 10/2023 | Patel | A61B 5/08 |

FOREIGN PATENT DOCUMENTS

| | | | |
|---|---|---|---|
| WO | WO 2021/119743 | | 6/2021 |
| WO | WO 2021/253093 | A1 | 12/2021 |

OTHER PUBLICATIONS

Shaikh et al.; Machine diagnosis using acoustic analysis: a review; Sep. 14, 2021; IEEE (Year: 2021).*

Jennifer Chu “Artificial Intelligence Model Detects Asymptomatic Covid-19 Infections through Cellphone-recorded Coughs” MIT News Office Oct. 29, 2020 7 Pgs.

BioIntelliSense “BioIntelliSense Announces FDA Clearance of the BioSticker, the First Single-Use Medical Device Enabling 30 Days of Continuous Vital Signs Monitoring” BioIntelliSense, Inc. Jan. 28, 2020 2 Pgs.

Food and Drug Administration “COVID-19 Test Basics” 2020 5 Pgs.

“How Amazon Transcribe Works” Amazon.com 2023 2 Pgs.

Kurt Schlosser “Seattle Teen Entrepreneurs Sell their Health-tech Startup and take a Break from College” GeekWire May 11, 2021 8 Pgs.

* cited by examiner

Data set (DS1) of phoneme or phoneme-like voice recording regions, annotated with ground truth label of phoneme and/or other label(s) related to characteristic of interest (VC). In pictured incarnation this VC is a binary status, and corresponding label is y for recording with VC, n for not (a.). In other incarnations VC can be non-binary - for ex. phoneme designation - with corresponding label - for ex. phoneme abbreviation. In all incarnations labels need not be discrete values - for ex. y/n or phoneme abbreviations - and could be more complex - for ex. likelihood scores. Machine learning model (ML1) is trained using DS1 to recognize the presence of VC (b.). After training, when ML1 is given an input in the format of the elements of DS1 it will output a prediction related to VC: such as Yes or No presence, or a likelihood score (c.).

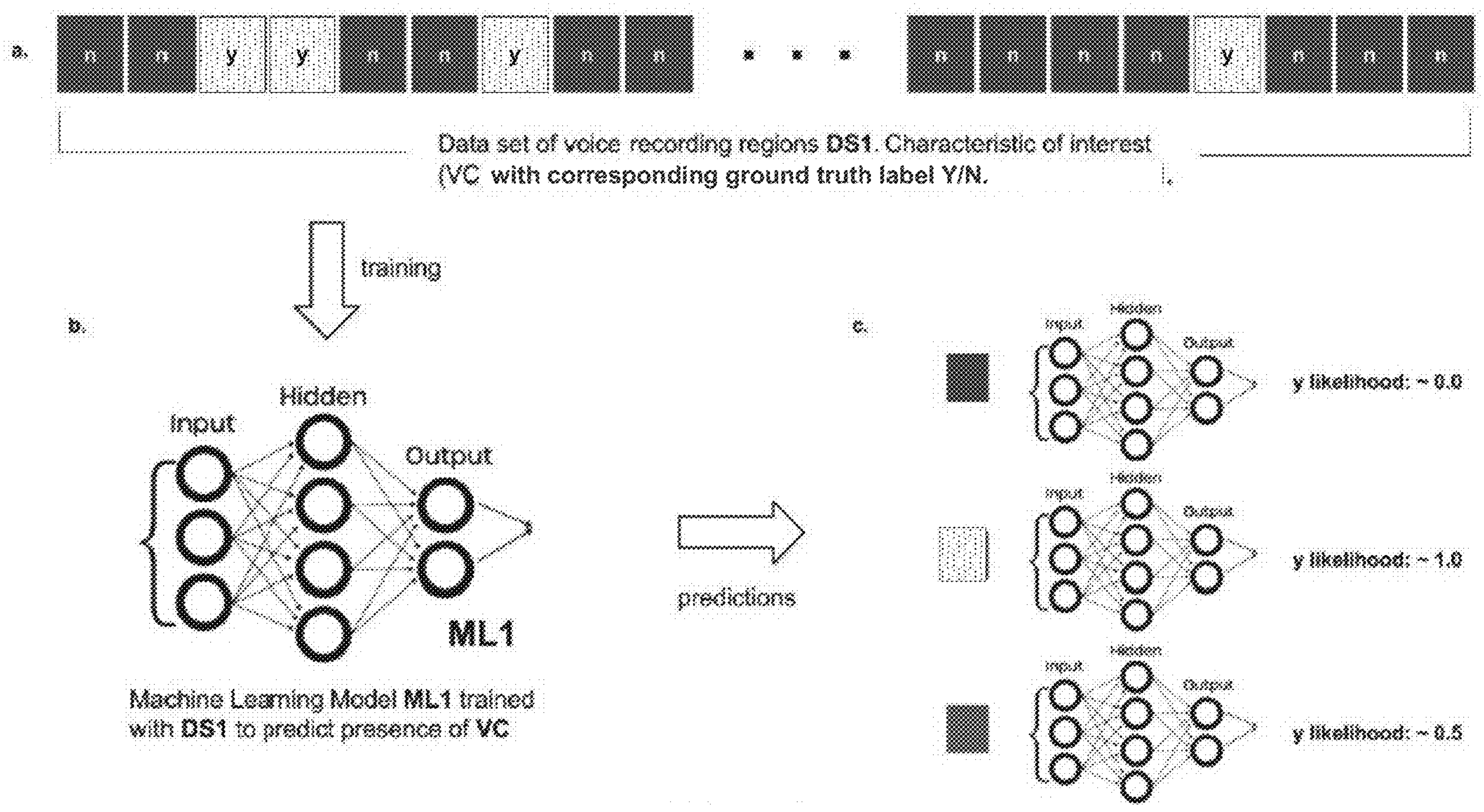

Fig. 3

Data set (DS2) of voice audio recording files with specific regions annotated with ground truth label of phoneme and/or other label(s) related to characteristic of interest VC (a. (see Figure 3.) Machine learning model (ML2) is created using ML1 and approaches such as sliding window convolutional neural networks, and trained using DS2 to recognize regions within an audio file that fulfill specific conditions of ML1's output related to VC (see Figure 3.) (b.). After training, when ML2 is given an input in the format of the elements of DS2 it will output a prediction consisting of the bounding timestamps of such regions, with labels based on VC such as Yes or No, or a likelihood score - notably even in the case where the input has no pre-existing labels (c.).

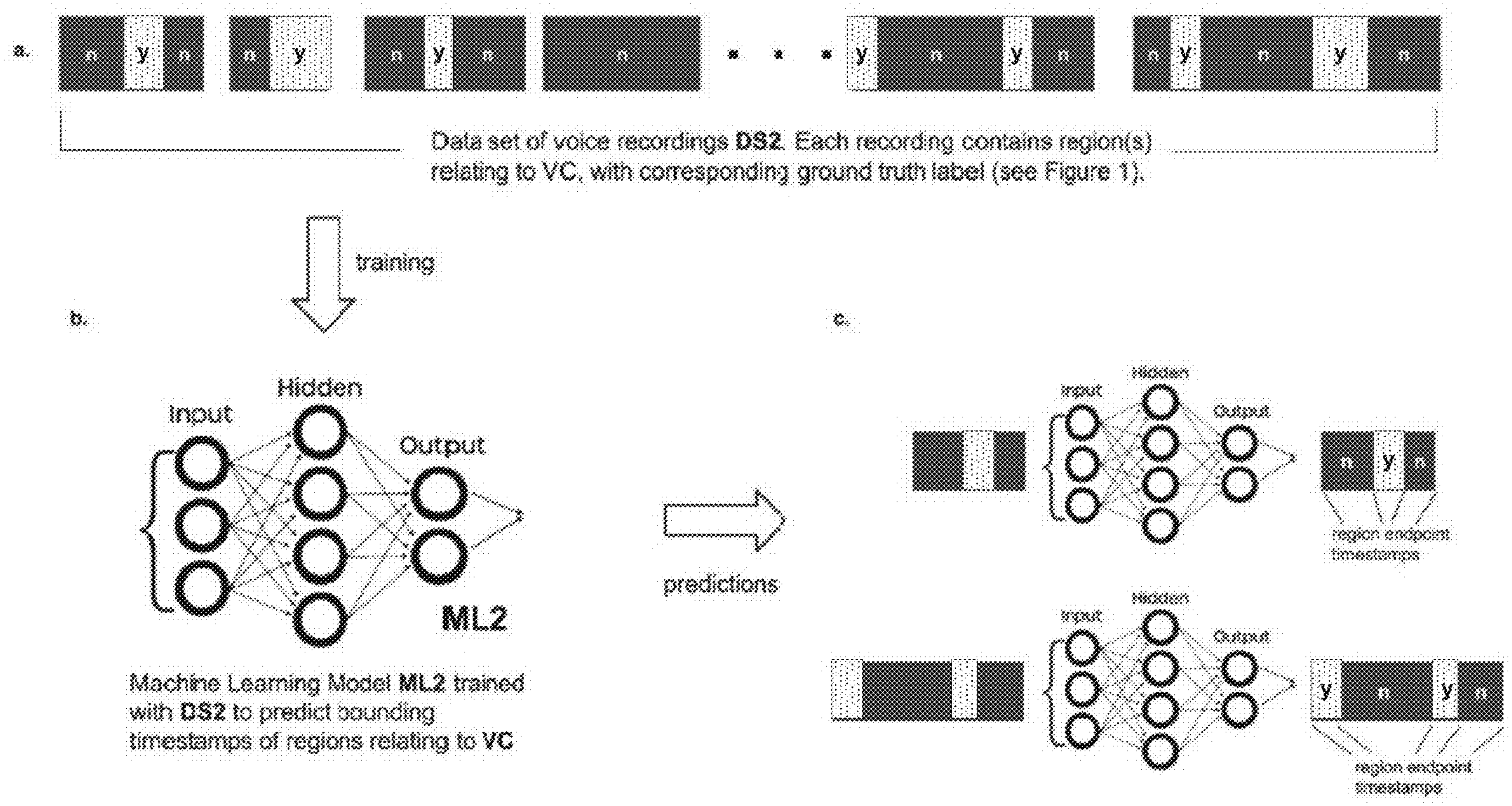

Fig. 4

Fig. 5

Data set (DS3) of voice audio recording files, annotated with ground truth label(s) related to a specific vocal audio property of final interest, VC-P. In pictured incarnation this VC-P is a binary status, and corresponding label is Y for recording with VC-P, N for not (a.). In other incarnations VC-P can be non-binary - for ex. one of a list of values such as covid-negative, covid-positive-symptomatic, covid-positive-asymptomatic . In all incarnations labels need not be discrete values - for ex. Y/N or covid status - and could be more complex - for ex. likelihood scores. Machine learning model (ML2) is created based upon ML1 designed to detect regions within an audio file that fulfill specific conditions of ML1's output related to VC (see Figure 3.) and additionally trained as necessary (see Figure 4.) When ML2 is given an input in the format of the elements of DS3 (b.) it will output a prediction of the bounding timestamps for each region with corresponding labels, such as Yes or No, or a likelihood score, while preserving the labels relating to VC-P in the input DS3 format file (c.). Regions passing ML2 prediction for VC are extracted into seperate audio files, each tagged with all associated labels. Thus extracted files are then aggregated to create a new data set (DS4).

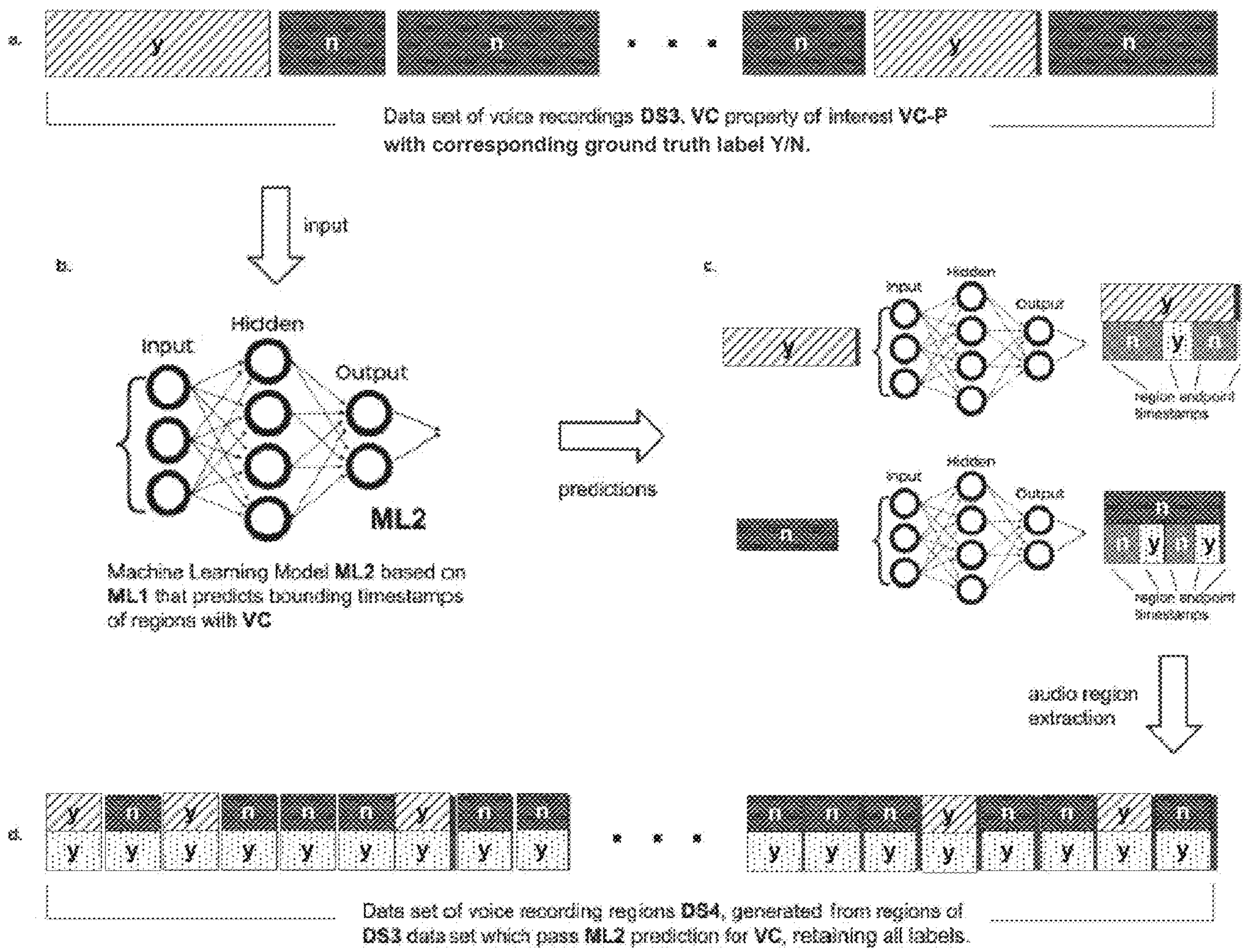

Data set (DS4) set of voice recording regions generated from regions of DS3 dataset which pass ML2 prediction for VC, annotated with labels regarding both VC and VC-P (see Figure 5.). In pictured incarnation both VC and VC-P are binary statuses, and corresponding labels are binary Yes/No values as well (a.). In other incarnations these can be non-binary. In all incarnations labels need not be discrete values and could be more complex, for ex. likelihood scores. Machine learning model (ML3) is trained using DS4 to recognize the presence of VC-P (b.). After training, when ML3 is given an input in the format of the elements of DS4, whether annotated or not, it will output a prediction related to VC-P: such as Yes or No presence, or a likelihood score (c.).

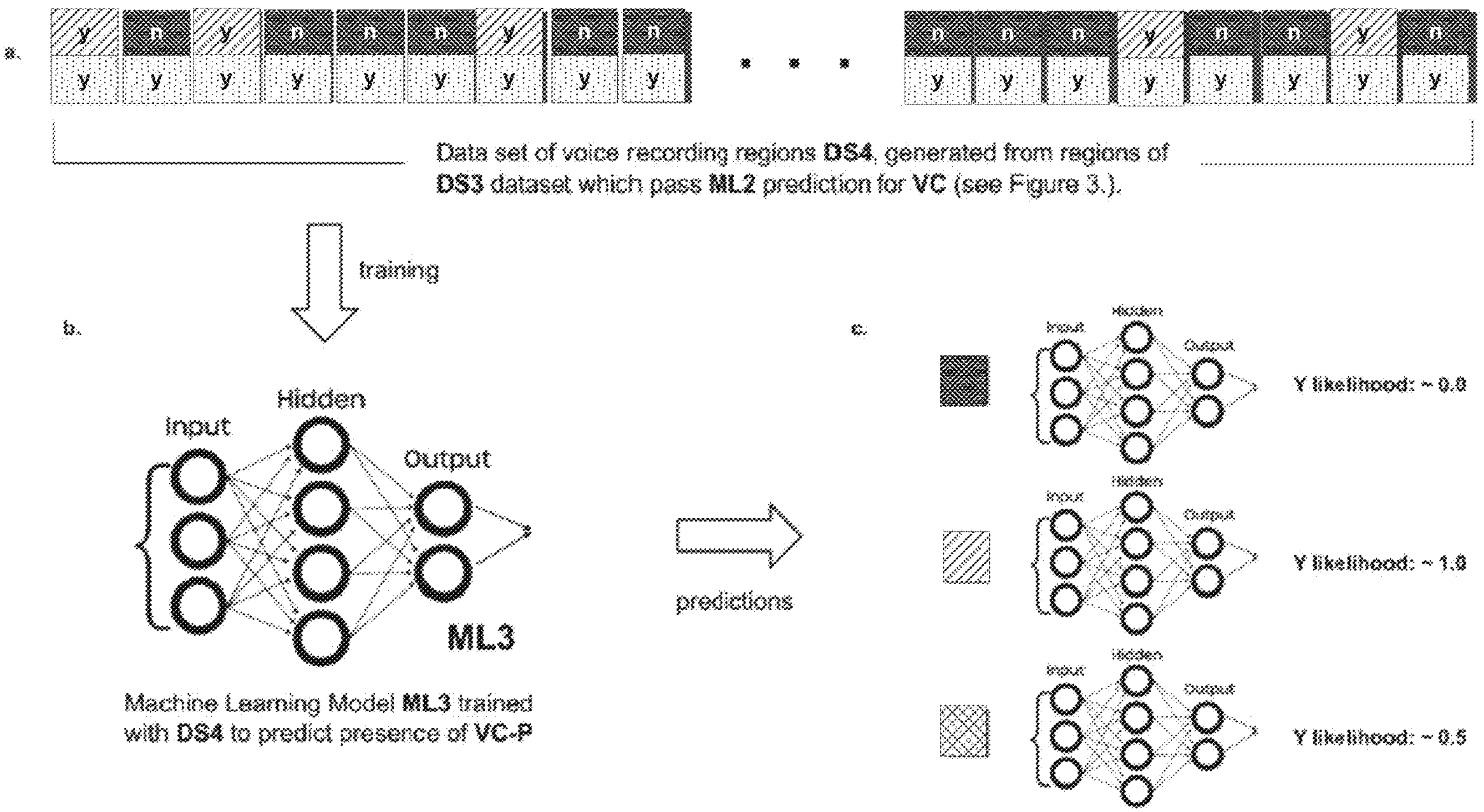

Fig. 6

Final machine learning model (ML+) is created as a composite of ML2 and ML3 (see Figures 5 and 6) , and can be further trained / validated by using data sets in the format of DS3 (see Figure 5.) (a.). When ML+ (b.) is given an input in the format of the elements of DS3 sans ground truth annotation, it will output a prediction related to VC-P, such as Yes or No presence, or a likelihood score (c.). When ML+ is given input it will first extract region(s) which pass ML2 prediction for VC and then each such region is input into ML3. Results of these such ML3 predictions are utilized to determine output prediction of ML+ related to VC-P; such as Yes or No presence, or a likelihood score (c.). As such the performance of ML+ can be improved over time by direct training via data sets in the form of DS3, or through independant improvements in ML1, ML2, or ML3, as describe (see Figures 3-6.)

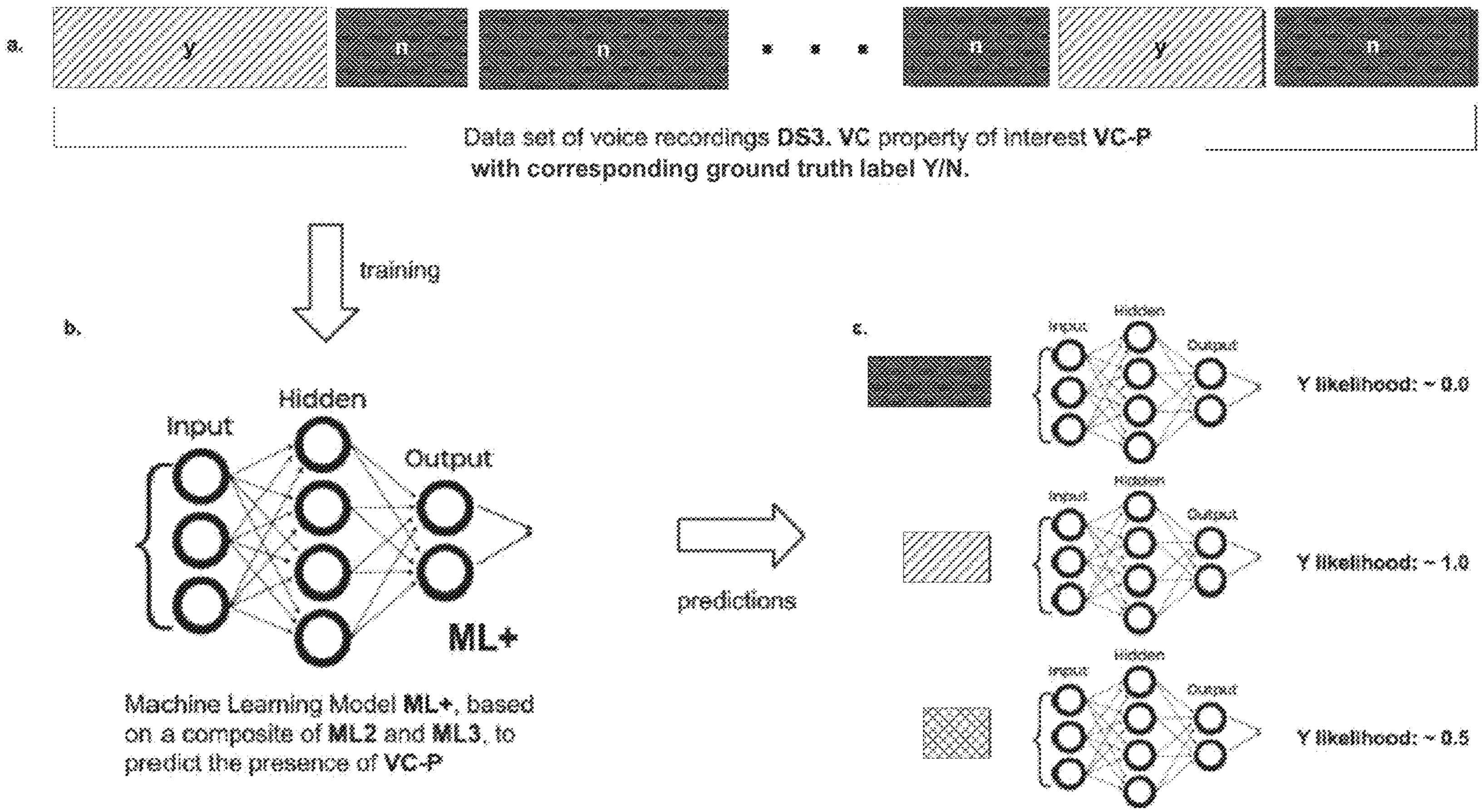

Fig. 7

An example final machine learning model (ML+) utilizing three different ML2 / ML3 model pairs: one pair based on the voiced bilabial nasal sound <M>, another on the phoneme <ou>, and another on coughs. In this example scenario the respective ML2 models identify and extract 2, 3, and 1 segments respectively (a.), and pass them into their associated ML3 models for testing. The VC-P prediction results for each segment (b.), which may be Yes or No presence, or a likelihood score, are then combined in a particular manner unique to this incarnation of ML+, to result in a final VC-P prediction (.c), which may be Yes or No presence, or a likelihood score. Other embodiments of ML+ could use one or many different ML2 / ML3 pairs, and could be based on segmentation types other than vocal phonemes.

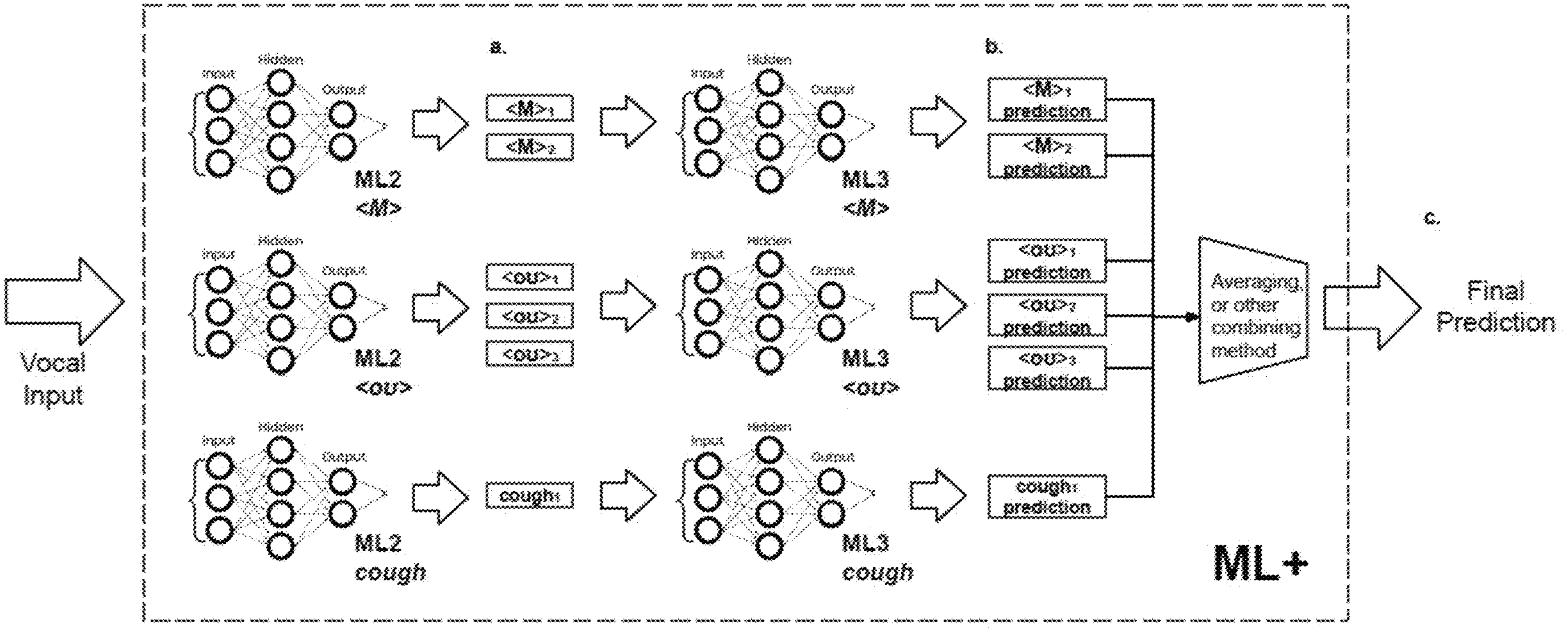

Fig. 9

MACHINE LEARNING MODEL BASED CONDITION AND PROPERTY DETECTION

RELATED APPLICATIONS

The present application claims the benefit of and priority to a Provisional Patent Application Ser. No. 63/194,018 filed on May 27, 2021, and titled “Condition and Media Property Prediction via Machine Learning Model Based Temporal Segmentation of Media,” which is hereby incorporated fully by reference into the present application.

BACKGROUND

Condition and property detection, such as various types of diagnostics for instance, may be performed in a variety of ways that can differ considerably depending on the condition or property serving as the subject of analysis, but often rely on manual processes. As one example, medical diagnostics often require extraction and testing of a blood or tissue sample, or expert review and interpretation of images or test results generated by sophisticated testing equipment such as computerized tomography (CT) or magnetic resonance imaging (MRI) scanners, electrocardiogram (ECG) machines, and the like. As another example, diagnostics performed on industrial equipment or other machines typically require human inspection, or at the very least review of sensor data by a trained human technician. Despite the diversity of the diagnostic techniques in use, a common element among many is the need for a human having some level of expertise to participate in the process. However, given the costliness of such human involvement, there exists a need in the art for automated solutions capable of inferentially interpreting diagnostic data.

BRIEF DESCRIPTION OF THE DRAWINGS

FIG. 3 illustrates a process for generating a dataset for use in training a first stage of a ML model for performing condition and property detection, according to one implementation;

FIG. 4 illustrates a process for training a first stage of a ML model for performing condition and property detection, according to one implementation;

FIG. 5 illustrates a process for generating a dataset for use in training a second stage of a ML model for performing condition and property detection, according to one implementation;

FIG. 6 illustrates a process for training a second stage of a ML model for performing condition and property detection, according to one implementation;

FIG. 7 illustrates an exemplary ML model trained to perform condition and property detection, according to one implementation;

FIG. 9 illustrates an exemplary ML architecture for performing condition and property detection in which multiple ML model pipelines having different first and second stages are utilized in parallel, according to one implementation.

DETAILED DESCRIPTION

Figure 1:
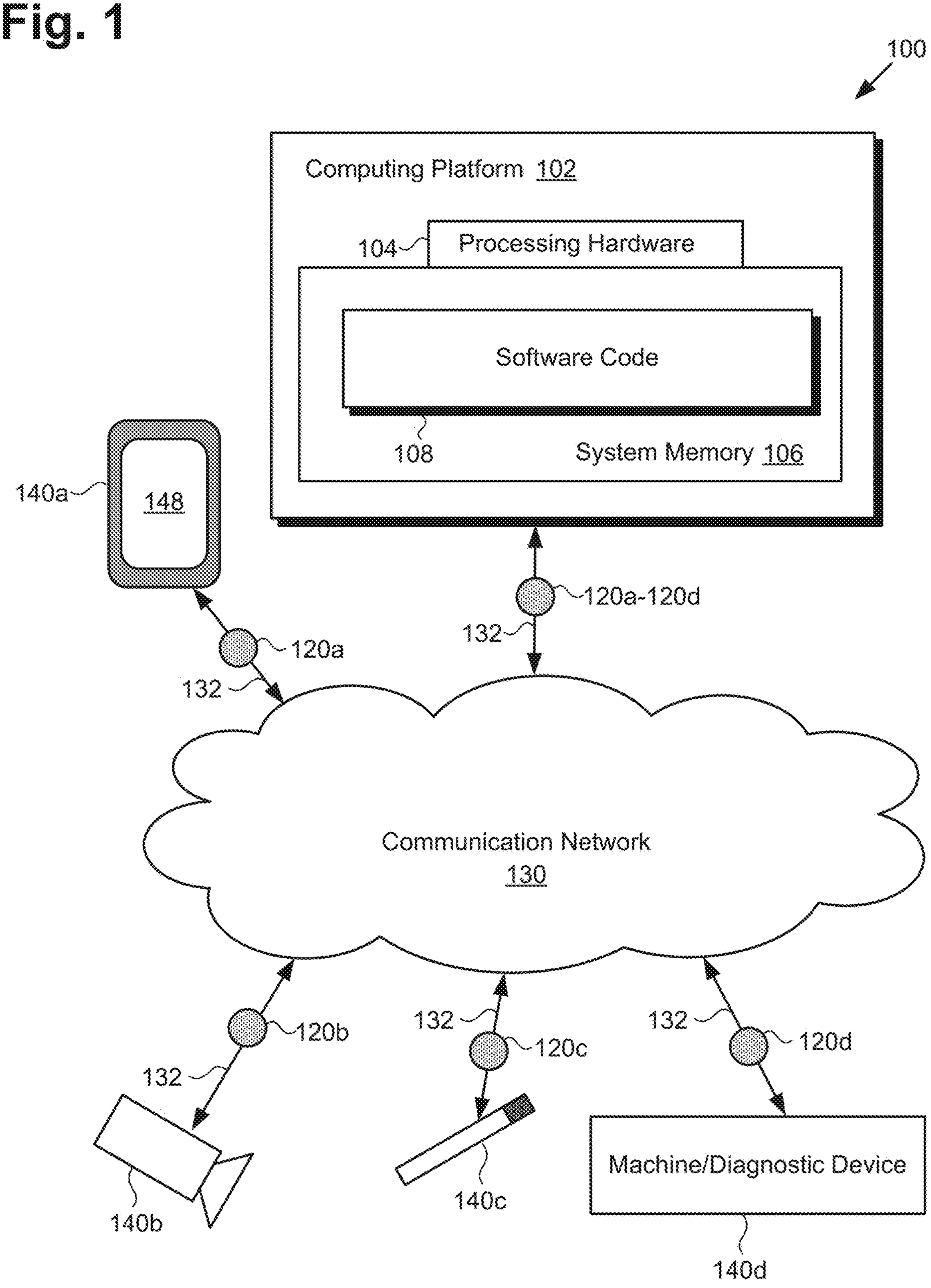
FIG. 1 shows a diagram of an exemplary system for performing machine learning (ML) model based condition and property detection, according to one implementation.

The following description contains specific information pertaining to implementations in the present disclosure. One skilled in the art will recognize that the present disclosure may be implemented in a manner different from that specifically discussed herein. The drawings in the present application and their accompanying detailed description are directed to merely exemplary implementations. Unless noted otherwise, like or corresponding elements among the figures may he indicated by: like or corresponding reference numerals. Moreover, the drawings and illustrations in the present application are generally not to scale, and are not intended to correspond to actual relative dimensions.

The present application discloses systems and methods for performing machine learning model based condition and property detection. It is noted that although the present condition and property detection solution is described below in detail by reference to FIGS. 3, 4, 5, 6, 7, 8, and 9 illustrating an exemplary use case in which a dataset including time-based audio of a human voice is used to predict the presence of an infectious disease marker, the present novel and inventive principles may be advantageously applied to various types of data to predict a wide variety of properties of interest. For instance, the present concepts can be readily adapted for use with substantially any type of dataset or data stream that can be granulized into tagged segment types, such as time-based media in the form of audio, video. audio-video (AV) content, or time-based diagnostic test data such as electrocardiogram. (ECG) data or electroencephalogram (EEG) data, to name a few examples. Specific use cases for the present novel and inventive concepts may include the operating performance of machinery such as home appliances, industrial equipment, ventilation systems, and vehicles, for instance. Examples of additional medical applications may include prediction of non-infectious disease states, prediction of chronic medical conditions such as dementia and schizophrenia, prediction of the presence of or recovery from musculoskeletal injury, immune system status, and stroke status, again to name merely a few examples.

Specific example use cases for the present novel and inventive concepts may include using video to predict early onset Alzheimer’s disease or Parkinson’s disease, or to predict a leg injury in a subject, for instance, based on walking or other movement by the subject. Alternatively, or in addition, video may be used to predict that a subject has had a stroke based on upper body movements or facial movements or expressions by the subject. As yet another alternative, or additionally, AV content or audio content may be used to diagnose malfunction of an appliance, such as a washing machine, tip or the need to replace a timing belt or other drive component of a car. Nevertheless, it is emphasized that any particular use case described or alluded to in the present application is not to be interpreted as limiting.

In some implementations, the systems and methods disclosed by the present application may be substantially or fully automated. As used in the present application, the terms “automation,” “automated,” and “automating” refer to systems and processes that do not require the participation of a human user, such as a human system administrator.

Although, in some implementations, an engineer or medical professional may review the performance of the automated systems operating according to the automated processes described herein, that human involvement is optional. Thus the processes described in the present application may be performed under the control of hardware processing components of the disclosed systems.

It is noted that the present media property prediction solution is machine learning model based. As defined in the present application, a "machine learning model," or "ML model," refers to a mathematical model for making future predictions based on patterns learned from samples of data obtained from a set of trusted known matches and known mismatches, known as training data, Various learning algorithms can be used to map correlations between input data and output data. These correlations form the mathematical model that can be used to make future predictions on new input data. Such a predictive model may include one or more logistic regression models, Bayesian models, or artificial. neural networks (NNs), for example. In addition, machine learning models may be designed to progressively improve their performance of a specific task.

A NN is a type of machine learning model in which patterns or learned representations of observed data are processed using highly connected computational layers that map the relationship between inputs and outputs. A "deep neural network" (deep NN), in the context of deep learning, may refer to a NN that utilizes multiple hidden layers between input and output layers, which may allow for learning based on features not explicitly-defined in raw data. As used in the present application, a feature labeled or described as a NN refers to a deep neural network. In various implementations, NNs may be utilized to perform image processing, audio processing, or natural-language processing, for example.

FIG. 1 shows exemplary system. 100 for performing ML model based condition and property detection, according to one implementation. As shown in FIG. 1, system 100 includes computing platform 102 having processing hardware 104 and system memory 106 implemented as a non-transitory storage medium. According to the present exemplary implementation, system memory 106 stores software code 108 which may include one or more ML models.

As further shown in FIG. 1, system 100 is implemented within a use environment including user systems 140*a*, 140*b*, 140*c*, and 140*d* (hereinafter "user systems 140*a*-140*d*") providing respective datasets 120*a*, 120*b*, 120*c*, and 120*d* (hereinafter "datasets 120*a*-120*d*"), which may include time-based media for example, to system 100 via communication network 130. ALSO shown in FIG. 1 are display 148 of user system 140*a*, and network communication links 132 of communication network 130 interactively connecting system 100 with user systems 140*a*-140*d*.

Although the present application refers to software code 108 as being stored in system memory 106 for conceptual clarity, more generally, system memory 106 may take the form of any computer-readable non-transitory storage medium. The expression "computer-readable non-transitory storage medium", as used in the present application, refers to any Medium excluding a carrier wave or other transitory signal that provides instructions to processing hardware 104 of computing platform 102 or to respective processing hardware of user systems 140*a*-140*d*. Thus, a computer-readable non-transitory storage medium may correspond to various types of media, such as volatile media and non-volatile media, for example. Volatile media may include dynamic memory, such as dynamic random access memory (dynamic RAM), while non-volatile memory may include optical, magnetic, or electrostatic storage devices. Common forms of computer-readable non-transitory storage media include, for example, optical discs such as DVDs, RAM, programmable read-only memory (PROM), erasable PROM (EPROM), and FLASH memory.

Processing hardware 104 of system 100 may include multiple hardware processing units, such as one or more central processing units, one or more graphics processing units, and one or more tensor processing units, one or more field-programmable gate arrays (FPGAs), custom are for machine-learning training or inferencing, and an application programming interface (API) server, for example. By way of definition, as used in the present application, the terms "central processing unit" (CPU), "graphics processing unit" (GPU), and "tensor processing unit" (TPU) have their customary meaning in the art. That is to say, a CPU includes an Arithmetic Logic Unit (ALU) for carrying out the arithmetic and logical operations of computing platform 102, as well as a Control Unit (CU) for retrieving programs, such as software code 108, from system memory 106, while a GPU may be implemented to reduce the processing overhead of the CPU by performing computationally intensive graphics or other processing tasks. A TPU is an application-specific integrated circuit (ASIC) configured specifically for artificial intelligence (AI) processes such as machine learning.

Although FIG. 1 depicts single computing platform 102, system 100 may include one or more computing platforms corresponding to computing platform 102, such as computer servers for example, which may be co-located, or may form an interactively linked but distributed system, such as a cloud-based system, for instance. As a result, processing hardware 104 and system memory 106 may correspond to distributed processor and memory resources within system 100. In one such implementation, computing platform 102 may correspond to one or lore web servers accessible over a packet—switched network such as the Internet, for example. Alternatively, computing platform 102 may correspond to one or more computer servers supporting a wide area network (WAN), a local area network (LAN), or included in another type of private or limited distribution network. Furthermore, in some implementations, system 100 may be implemented virtually, such as in a data center. For example, in some implementations, system 100 may be implemented in software, or as virtual machines.

It is further noted that, although user systems 140*a*-140*d* are shown variously as smartphone computer 140*a*, video camera 140*b*, microphone 140*c*, and machine or diagnostic device 140*d*, in FIG. 1, those representations are provided merely by way of example. In other implementations, user systems 140*a*-140*d* may take the form of any mobile or stationary devices capable of obtaining datasets 120*a*-120*d*. When implemented as smart devices, for example, user systems 140*a*-140*d* may be any suitable mobile or stationary computing devices or systems that implement data processing capabilities sufficient to provide a user interface, support connections to communication network 130, and implement the functionality ascribed to user systems 140*a*-140*d* herein. That is to say, in other implementations, one or more of user systems 140*a*-140*d* may take the form of a desktop computer, laptop computer, tablet computer, or an implanted medical device, such as a. pacemaker or pump, to name a few examples. In addition, or alternatively, in some implementations one or more of user systems 140*a*-140*d* may take the form of a smart wearable device, such as a smartwatch, for example. It is also noted that display 148 may take the for n of a liquid crystal display (LCD), light-emitting diode (LED) display, organic light-emitting diode (OLED) display, quantum dot (QD) display, or any other suitable display screen that perform a physical transformation of signals to light.

Figure 2:
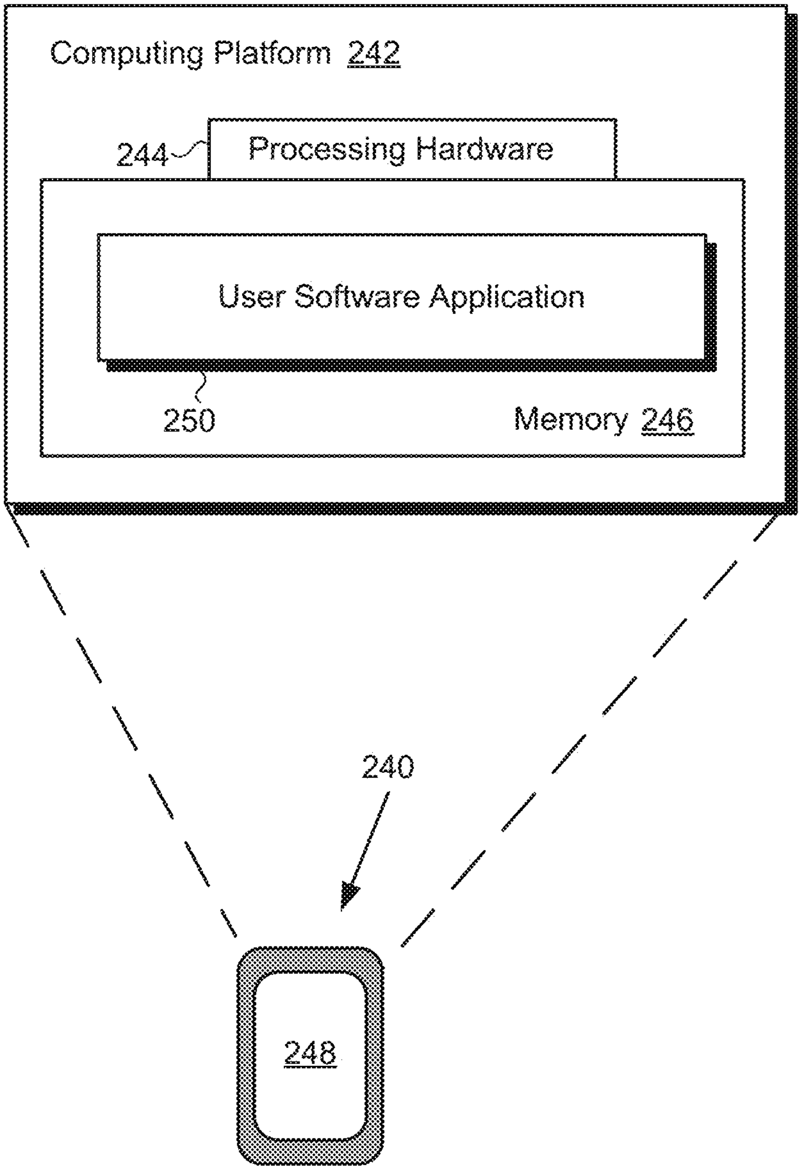
FIG. 2 shows a diagram of another exemplary implementation of a system for performing ML model based condition and property detection.

FIG. 2 shows another exemplary system, i.e., user system 240, for performing ML model based condition and property detection, according to another implementation. As shown in FIG. 2, user system 240 includes computing platform 242 having processing hardware 244, memory 246 implemented as a nor-transitory storage medium storing user software application 250, and display 248. It is noted that, in various implementations, display 248 may be physically integrated with user system 240 or may be communicatively coupled to but physically separate from user system 240. For example, where user system 240 is implemented as a smartphone, laptop computer, or tablet computer, display 248 will typically he integrated with user system 240. By contrast, where user system 240 is implemented as a desktop computer, display 248 may take the form of a monitor separate from computing platform 242 in the form of a computer tower.

User system 240 corresponds in general to any or all of user systems 140*a*-140*d* in FIG. 1, while display 248 corresponds in general to display 148. Thus, user systems 140*a*-140*d* and display 148 may share any of the characteristics attributed to user system 240 and display 248 by the present disclosure, and vice versa. That is to say, like display 148, display 248 may take the form of an LCD, LED display, OLED display, or QD display, for example. Moreover, although not shown in FIG. 1, one or more of user system 140*a*-140*d* may include features corresponding respectively to computing platform 242, processing hardware 244, and memory 246 storing user software application 250.

User system processing hardware 244 may include multiple hardware processing units, such as one or more CPUs, ogre or more GPUs one or more TPUs, and one or more FPGAs, for example, as those features are defined above.

With respect to user software application 250, it is noted that in some implementations, user software application 250 may be a thin client application of software code 108, in FIG. 1. In those implementations, user software application 250 may enable user system 240 to obtain any of datasets 120*a*-120*d*, and to provide that dataset to system 100 for processing. However, in other implementations, user software application 250 may include substantially all of the features and functionality of software code 108. That is to say, in some implementations, user system 240 may perform any or all of the operations attributed to system 100 by the present disclosure.

According to the exemplary implementation shown in FIG. 2, user software application 250 is located in memory 246 of user system 240, subsequent to transfer of user software application 250 to user system 240 via an external flash drive or dongle, or over a packet-switched network, such as the Internet, for example. Once present on user system 240, user software application 250 may be persistently stored in memory 246 and may be executed locally on user system 240 by user system processing hardware 244.

System 100 and user system 240 are further described below by reference to FIGS. 3, 4, 5, 6, 7, 8, and 9, which illustrate a specific example use case wherein audio properties of a dataset including time-based media in the form of recorded human vocalizations are used to predict the presence of an infectious disease, in one particular use case the presence of a. respiratory illness, such as influenza or Coronavirus Disease 2019 (COVID-19).

By way of background, existing voice-based methods for detecting COVID-19 require analysis of pre-identified utterances of interest, such as coughs, manual segmentation of existing ground truth audio data sets by human researchers in order to isolate such utterances, and test subjects who are required to perform these specific forced utterances, e.g., forced coughing. These conventional approaches hamper the creation of an effective voice-based COVID-19 detector for several reasons. For example, by limiting analysis to pre-identified utterances of interest the possible solutions obtainable are restricted to only those that can arise from preconceived hypotheses, thereby hindering serendipity. In addition, manual segmentation of data prevents end-to-end processes from being automated, which impedes the rapid iterations and convergence typically made possible by machine-learning approaches. Moreover, requiring collection of uncommon utterances limits data collection. opportunities to laboratory scenarios or coached data collection initiatives, while requiring collection of symptom-based utterances restricts opportunities to collect data from asymptomatic disease carriers.

In the exemplary use case of a novel infectious disease, such as COVID-19, for which an extensive knowledge base is under development, the prediction solution disclosed in the present application overcomes the aforementioned deficiencies in the conventional art by implementing a multi-step ML model based process that can predict disease presence by automatically segmenting unstructured vocal sample data into normalized datasets, each data element being of specific audio segment types that are determined to be optimal for prediction of COVID-19 infection, and using those datasets to train disease predictors to be more flexible and precise than conventional approaches allow.

For example: if it is known that analysis of the audio properties of a certain type of vocal utterance, such a "mmmmm," for instance, is most effective for prediction of COVID-19, the present prediction solution can take a dataset of unstructured voice samples that are tagged with COVID-19 status (collected from hospitals, for example), extract the "mmmmm" utterance segments into a normalized dataset that retains the corresponding COVID-19 status tags, and use this dataset to train and deploy a composite ML model that can predict COVID-19 status, based upon input of an unstructured vocal sample. It is noted that the vocal utterance identified in the present application as "mmmmm" refers to a sustained consonantal sound known formally as the "voiced bilabial nasal," identified by the symbol (m) in the International Phonetic Alphabet. That is to say, the vocal utterance "mmmmm" is produced by sustaining the sound of the English letter "m" at the end of English word "them."

Although this example relies on prior knowledge that a segment type based on the "mmmmm" utterance would be useful for ML model based prediction of COVID-19, the present prediction process can be performed with various different segment types in parallel, such as isolating utterances of each vocal phoneme into separate datasets, for example, in order to determine which segment types are most effective for prediction of COVID-19. This may be advantageous in cases where no a priori or existing a posteriori knowledge exists, as well as for identifying segments which can expand data collection opportunities. For instance, a segment based on a phoneme sound such as "oΩ" would be collectible from normal speech (and thus amenable to ambient, passive data collection approaches), but a segment based on a coughing sound would only be collectible from people who are symptomatic or from those who are instructed to cough via a coached data collection process.

To illustrate the process outlined above in detail, consider the exemplary use case in which the objective is to create a voice-based predictor for COVID-19 based on input of normal speech, and that there is reason to believe that analysis of the vocal resonances in the sound "mmmmm" will be particularly useful for prediction of COVID-19. Under those circumstances the present prediction solution may proceed as follows:

1: Referring to FIG. 3, beginning with a dataset of various vocal utterances, including examples of the sound "mmmmm" as well as many other sounds, where each data. element is tagged with a label that specifies whether the element Is or Is Not "mmmmm." This initial dataset (hereinafter "DS1" as identified in FIG. 3) can either be acquired or created. DS1 may then be used to train a ML model (hereinafter "ML1" as also identified in FIG. 3) which takes as input audio segment elements in the format of DS1 and outputs a likelihood value for the input element being "mmmmm," based on techniques such as spectrogram analysis, Hidden Markov models, and the like. This is illustrated by FIG. 3 with "mmmmm" being the characteristic of interest (hereinafter denoted by "VC"). It is noted that, in some implementations, ML1 may be a feature of software code 108 of system 100, or of user software application 250 of user system 240. DS1 may be acquired or created, and may be used to train ML1, by software code 108, executed by processing hardware 104 of system 100, or by user software application 250, executed by user system processing hardware 244.

2: Referring to FIG. 4, a new ML model (hereinafter "ML2" as identified in FIG. 4) may be created, which can predict the bounding timestamps of segments within an input audio file that are Yes for VC, in this case the "mmmmm" sound, with sufficiently high likelihood. ML2 may be created based upon ML1 and machine learning techniques such as sliding window convolutions, where stride length may be a tunable hyperparameter of the model. ML2 can be trained using another dataset (hereinafter "DS2" as also identified in FIG. 4) of unstructured audio speech files having temporal segments tagged with VC status. As with DS1, DS2 can either be acquired or created. It is noted that ML2 may also be a feature of software code 108 of system 100, or of user software application 250 of user system 240. ML2 may be created, and may be trained using DS2, by software code 108, executed by processing hardware 104 of system 100, or by user software application 250, executed by user system processing hardware 244.

3: Referring to FIG. 5, another dataset (hereinafter "DS3" as identified in FIG. 5) may be acquired, which cc ns elements that are unstructured vocal recordings annotated with ground truth data of the recorded person's COVID-19 status. Datasets such as DS3 already exist from hospitals, universities and the like. The elements of DS3 can be used as inputs into ML2, which identifies audio segment regions that are "mmmmm," which can then be extracted into a new a dataset (hereinafter "DS4" as also identified in FIG. 5), which includes elements that not only are "mmmmm" but each of which inherits the COVID-19 status tag from the recording that it was extracted from. This is illustrated by FIG. 5, with COVID-19 status denoted as VC-P. Like procedures 1 and 2 described above, the present procedure may be performed by software code 108, executed by processing hardware 104 of system 100, or by user software application 250, executed by user system processing hardware 244.

4: Referring to FIG. 6, dataset DS4 may be used to train another ML model (hereinafter "ML3" as identified in FIG. 6) that outputs a prediction for the likelihood of COVID-19 given an input in the format of the elements of DS4, "mmmmm" in this exemplary use case. ML3 can be created and trained without prior knowledge. However, efficacy may be improved by creating ML3 based on existing knowledge of acoustic biomarkers likely to be relevant for unique and specific prediction of COVID-19, even amongst asymptomatic carriers, and audio processing techniques such as Fast Fourier Transforms and Mel-frequency Cepstrum analysis. Examples of such acoustic biomarkers may be manifestations of one or more of COVID-19 related neuromuscular vocal cord impairment, respiratory degradation, or changes in intonation, to name a few. It is noted that ML3 may also be a feature of software code 108 of system 100, or of user software application 250 of user system 240. Moreover, procedure 4 described above may be performed by software code 108, executed by processing hardware 104 of system 100, or by user software application 250, executed by user system processing hardware 244.

5: Referring to FIG. 7, the final ML model based COVID-19 predictor (hereinafter "ML+" as identified in FIG. 7) may be created based on a combination of the ML2 and ML3 models. It is noted that, in some implementations, ML+ may take the form of an integrated ML model having ML2 as a first, i.e., input stage, and having ML3 as a second, i.e., output stage. ML+ can take as input unstructured audio recording data (such as a person speaking normally into a mobile phone) and output a prediction of COVID-19 status, such as a likelihood score. ML+, which could be deployed via user software application 250, for example, is given input that it will first extract one or more region(s) which are predicted by ML2 to be of the "mmmmm" segment type. That or those region(s) may then be provided as input into ML3. The resulting ML3 COVID 19 status predictions can then be utilized to determine output of ML+ with respect to COVID-19 status: such as "Positive" or "Negative," or as a likelihood score. As a simple example, the likelihood predictions could be averaged to determine the ML+ output prediction, but a more complicated process could be utilized as well.

The performance of ML+ can be improved over time by direct training via datasets in the form of DS3, or through independent improvements in ML1, ML2, or ML3. In addition, any ground truth data from additional COVID-19 test results, such as polymerase chain reaction (PCR) tests for example, can be used to augment dataset DS3, and consequently refine ML3 and parameters, such as acceptable prediction likelihood thresholds, averaging processes used for multiple ML3 predictions in ML+, and the like. ML+ may be a feature of software code 108 of system 100, or of user software application 250 of user system 240. Moreover, procedure 5 described above may be performed by software code 108, executed by processing hardware 104 of system 100, or by user software application 250, executed by user system processing hardware 244.

As noted above, in some implementations, procedures 1 through 5 may be performed on system 100, while in other implementations procedures 1 through 5 may be performed on user system 240. However, in other implementations, ML+ may be deployed to user software application 250 on user system 240 after its creation on system 100. In still other implementations, ML+ may be deployed to system 100 after its creation elsewhere, and software code 108, when executed by processing hardware 104, may utilize that pre-existing ML+ to predict the respiratory infection (e.g., COVID-19) status using unstructured voice samples.

In the above-described case prior knowledge that the vocal resonances in the sound "mmmmm" would be particularly useful for prediction of COVID-19 was presumed. In the absence of such knowledge, or as a supplement to it, it is noted that procedures 1 through 4 can be used to generate multiple different instances of ML3 in parallel. In such an implementation, procedures 1 through 4 could be performed for each vocal phoneme instead of just the sound "mmmmm," for example, and the most efficacious vocal segment types for prediction of COVID-19 could be determined. This could be accomplished by creating DS1 datasets tagged with Yes/No for each of the different segment types, or all at once in a single non-binary segmenter via the procedures depicted in FIG. 3 and FIG. 4. This would lead to extracting datasets relating to each audio segment type in procedure 3, and so forth.

Figure 8:
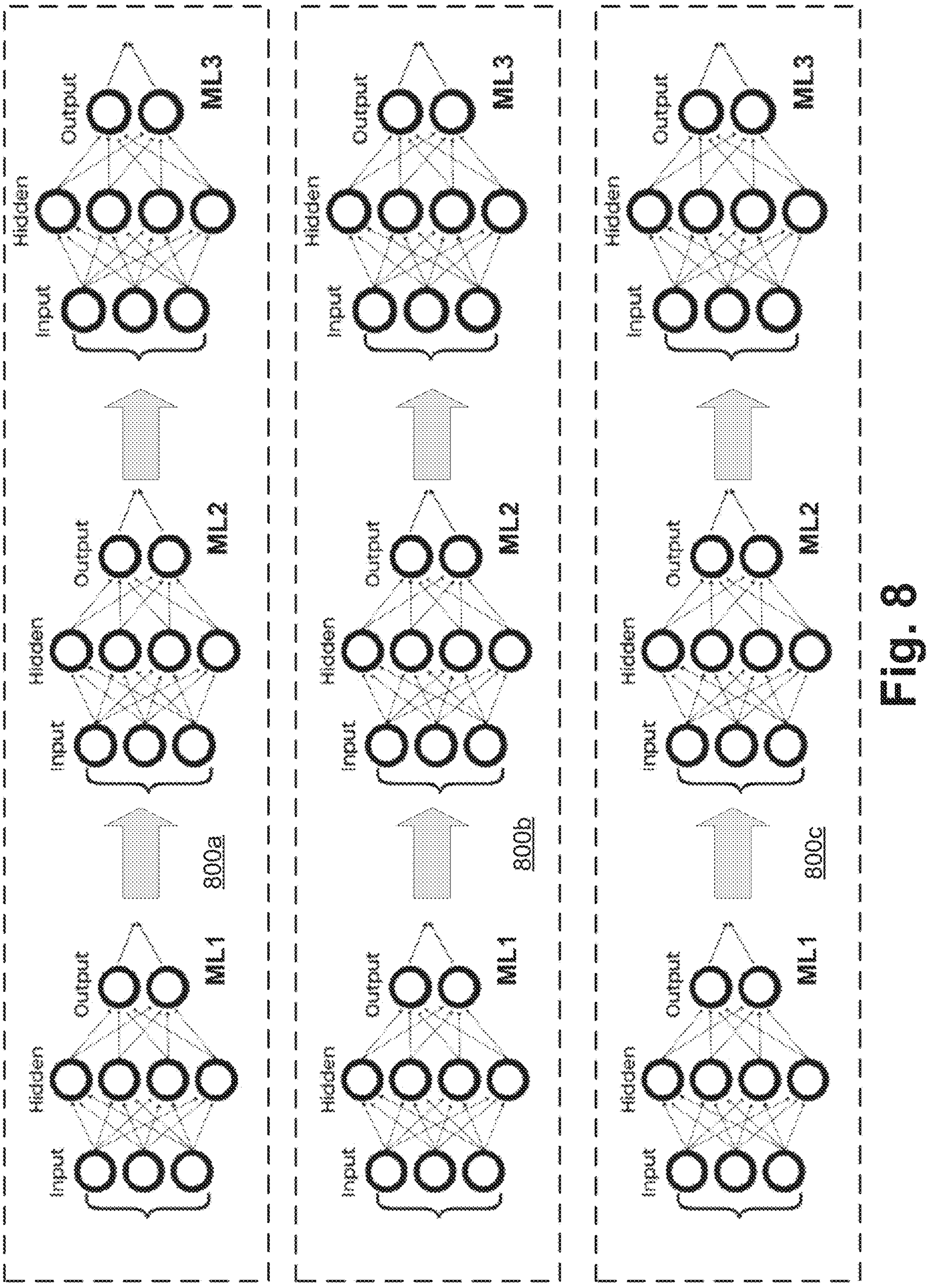
FIG. 8 illustrates an exemplary ML model for performing condition and property detection that includes multiple first and second stages, according to one implementation.

An example of generating multiple different instances of ML3 is shown in FIG. 8, in which each of machine learning pipelines 800*a*, 800*b*, and 800*c* produce different instantiations of ML3 independently of one another and in parallel. It is noted that although FIG. 8 shows three parallel machine learning pipelines 800*a*, 800*b*, and 800*c*, that representation is merely exemplary. In other use cases in which multiple instances of ML3 are generated, as few as two parallel machine learning pipelines, or more than three machine learning pipelines, may be employed.

As an example, in some implementations, ML+ can be enhanced as the result of the generation of multiple instances of ML3 using different instances of ML2 as shown in FIG. 8. For example, a version of ML+ finalized for deployment could make use of those parallel ML2 and ML3 portions of machine learning pipelines 800*a*, 800*b*, and 800*c* in any desired combination, as further shown in FIG. 9.

Because the process depicted in FIG. 8 and FIG. 9 does not require prior knowledge or presumption, it can be useful for the prediction of diseases and physical or mental conditions that may have different, novel, and unknown vocal or non-vocal signatures, as well as the determination of the vocal or other data segment types that are optimal for the prediction or diagnosis of such diseases and conditions. These may include non-infectious diseases and chronic conditions such as dementia, schizophrenia, and Parkinson's disease, for example. When informed consent is obtained, non-disease characteristics can be predicted through this process as well, such as biological sex, age, and stress level. Because non-disease factors such as increased stress level are correlated with diminished immune system function, the prediction process described above can result not only in the creation of effective predictors of disease, but also predictors of disease susceptibility.

Moreover, for the specific use case of diagnosing COVID19 and other infectious diseases, because the present ML model based diagnostic solution is configured to detect human manifestations of the disease state, it is agnostic, and therefore remains effective as a diagnostic tool, even when infectious vectors mutate. Thus, in contrast to rapid antigen tests for COVID-19, which are to some extent variant specific, and tend to fail when the severe acute respiratory syndrome coronavirus 2 (BARS-CoV-2) causing COVID-19 mutates, the present ML model based diagnostic solution can be expected to be, and remain, robustly reliable against viral sub-variants.

As an additional advantage with respect to acquisition and management of personally identifiable information (PII) or other sensitive personal information, in implementations in which ML+ is deployed to user software application 250, any PII acquired by user software application 250 may be sequestered on user system 240 and be unavailable to system 100 or other external agents.

Figure 10:
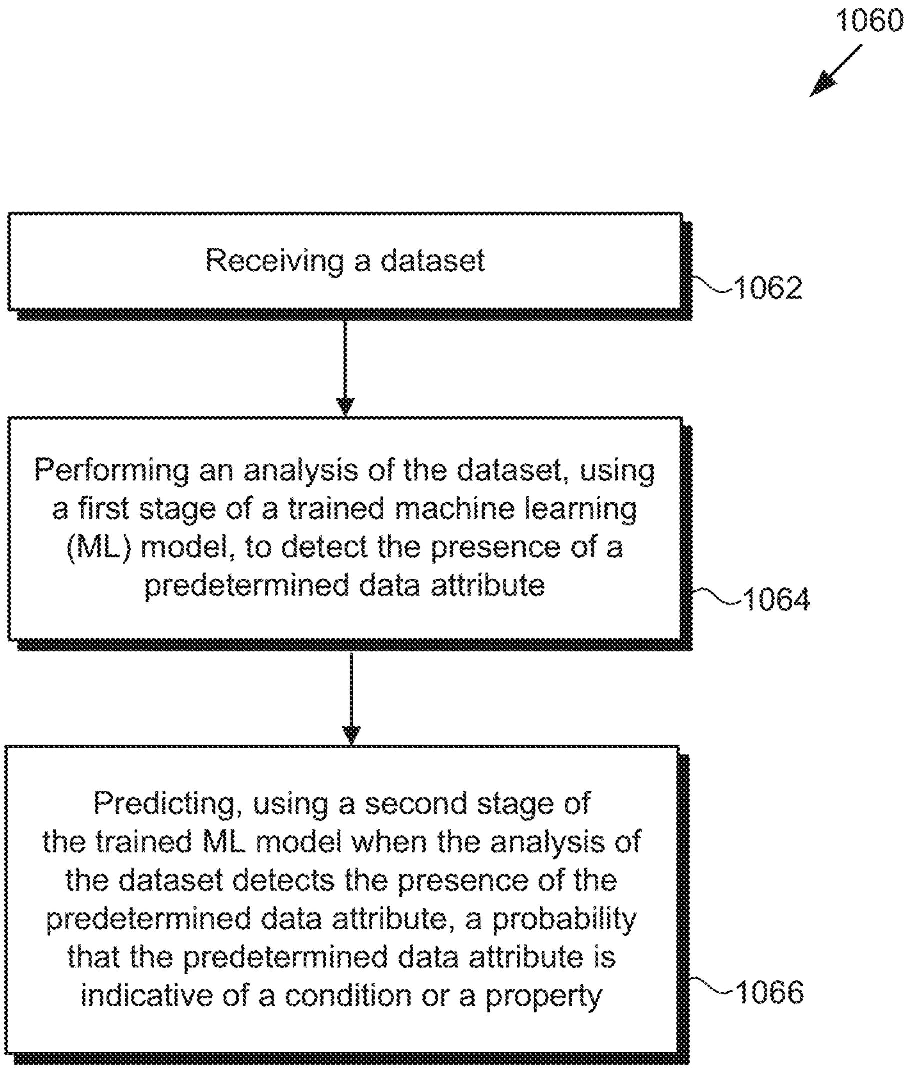
FIG. 10 shows a flowchart outlining an exemplary method for performing ML model based condition and property detection, according to one implementation.

The functionality of system 100, user system(s) 140*a*-140*d*/240, software code 108, and user software application 250 shown variously in FIGS. 1 and 2 will be further described by reference to FIG. 10. FIG. 10 shows flowchart 1060 presenting an exemplary method performing ML model based condition and property detection, according to one implementation, With respect to the method outlined in FIG. 10, it is noted that certain details and features have been left out of flowchart 1060 in order not to obscure the discussion of the inventive features in the present application.

Referring to FIG. 10 in combination with FIGS. 1 and 2 flowchart 1060 begins with receiving one of datasets 120*a*-120*d* (action 1062). As noted above, datasets 120*a*-120*d* may include a variety of different data types, including e-based media in the form of audio, video, AN content, sensor data, and test result data, to name a few examples. In some implementations, as shown in FIG. 1, the dataset received in action 1062 may be generated or obtained by one of respective user systems 140*a*/240, 140*b*/1240, 140*c*/240, or 140*d*/240, and may be received by system 100 from the one of respective user systems 140*a*/240, 140*b*/240, 140*c*/240, or 140*d*/240 via communication network 130 and network communication links 132. In those implementations, the dataset may be received in action 1062 by soft ode 108, executed by processing hardware 104 of computing platform 102.

Alternatively, and as noted above, in some implementations, the diagnostic processing of the one of datasets 120*a*-120*d* may be performed locally on one of respective user systems 140*a*/240, 140*b*/240, 140*c*/240, or 140*d*/240 In these implementations, the dataset received in action 1062 may be received by user software application 250, executed by user system processing hardware 244.

Flowchart 1060 further includes performing an analysis of the dataset received in action 1062, using a first stage, i.e., ML2 of trained ML model ML+, to detect the presence of a predetermined data attribute (action 1064). For example, in the case of the COVID-19 diagnostic procedure described above, processing hardware 104 may execute software code 108, or user system processing hardware 244 may execute user software application 250 to determine whether the dataset received in action 1062 includes the sound "mmmmm" and the bounding timestamps of regions that include that characteristic oaf interest.

Thus, in some implementations, the predetermined data attribute having its presence analyzed in action 1064 may audio attribute of the dataset received in action 1062. In implementations in which the predetermined data attribute is an audio attribute, that audio attribute may be derived from one or more of speech, a non-verbal utterance, or a pulmonary expulsion, such as a cough for example. Alternatively, or in addition, the predetermined attribute the predetermined data attribute having its presence analyzed in action 1064 may be a visual attributed in the form of a human tremor or tic.

Thus, in some implementations, processing hardware 104 may execute software code 108, or user system processing hardware 244 may execute user software application 250 to utilize a visual analyzer included as a feature of software code 108 or user software application 250, an audio analyzer included as a feature of software code 108 or user software application 250, or such a visual analyzer and audio analyzer, to perform the analysis of the received dataset in action 1064.

In various implementations, a visual analyzer included as a feature of software code 108 or user software application 250 may be configured to apply computer vision or other AI techniques to the dataset received in action 1062, or may be implemented as a NN or other type of ML model. Such a visual analyzer may be configured or trained to recognize physical movements and their frequency, for example.

An audio analyzer included as a feature of software code 108 or user so-are application 250 may also be implemented as a NN or other ML model. As noted above, in some implementations, a visual analyzer and an audio analyzer may be used in combination to the received dataset. It is noted that the received dataset will typically include multiple video frames, multiple audio frames, or multiple video frames and multiple audio frames. In some of those use cases, processing hardware 104 may execute software code 108, or user system processing hardware 244 may execute user software application 250 to perform the visual analysis of the received dataset, the audio analysis of the received dataset, or both the visual analysis and the audio analysis, on a frame-by-frame basis. That is to say, in various implementations, the analysis of the received dataset n action 1064 may be performed by software code 108, executed by processing hardware 104 of system 102, or by user software application 250, executed by user system processing hardware 244.

In some implementations, performing the analysis of the dataset in action 1064 may include detecting, using first stage ML2 of trained ML model ML+, one or more temporal segments of the received dataset that include the predetermined data attribute. In some implementations in which first stage ML2 of trained ML model ML+ is configured to detect one or more temporal segments of the received dataset that include the predetermined data attribute, first stage ML2 may be trained using a dataset, DS2, that has been annotated to identify the predetermined data attribute, to detect temporal segments of a test dataset that include the predetermined data attribute. As noted above, DS2 may be created or obtained by system 100 or user system(s) 140*a*-140*d*/240. In implementations in which DS2 is created by system 100 or user system(s) 140*a*-140*d*/240, DS2 may be generated by training another ML model to detect the presence of the predetermined data attribute in other test data, and using an output of that ML model to train yet another ML model to predict bounding timestamps for a temporal segment of that other test data that include the predetermined data attribute.

In some implementations, the training of first stage ML2 using DS2, the generation of DS2, or the generation of DS2 and the training of first stage ML2 using DS2, may be performed by software code 108, executed by processing hardware 104 of system 102, or by user software application 250, executed by user system processing hardware 244.

Flowchart 1060 further includes predicting, using second stage ML3 of trained ML model ML+ when the analysis of the dataset performed in action 1064 detects the presence of the predetermined data attribute, a probability that the predetermined data attribute is indicative of a condition or a property (action 1066). In some implementations in which second stage ML3 of trained model ML+ is used to predict the probability hat the predetermined data attribute is indicative of a condition, that condition may be one of a physical condition, a disease state, or a chronic medical condition, for example, as noted above. Alternatively and as further noted above, in other implementations in which second stage ML3 of trained ML model ML+ is used to predict the probability that the predetermined data attribute is indicative of a condition, that condition may be the operating performance of a machine, such as its output, energy consumption, heat generation, or overall efficiency, for example.

In implementations in which first stage ML2 of trained ML model ML+ is configured to detect one or more temporal segments of the received dataset that include the predetermined data attribute, predicting the probability that the predetermined data attribute is indicative of the condition or the property using ML3 in action 1066, may include predicting whether at least one of those one or more temporal segments including the predetermined data attribute is indicative of the condition or the property. In some of those implementations, second stage ML3 may be trained using a dataset, DS4, which has been annotated to correlate the predetermined data attribute with one of the condition or the property, to predict whether a temporal segment including the predetermined data attribute is indicative of the condition or the property.

Trained ML model ML+ may then be validated using validation data having a known ground truth, by delivering the validation data as an input to first stage ML2 and obtaining a prediction for the condition or the property as an output from second stage ML3, In some implementations, training of ML3, as well as validation of trained ML model ML+, may be perforated by software code 108, executed by processing hardware 104 of system 102, or by user software application 250, executed by user system processing hardware 244. It is noted that in various implementations, one or both of first stage ML2 and second stage ML3 of trained ML model ML+ may be trained using a federated learning process, as known in the art. It is further noted that with respect to the method outlined by flowchart 1060, in some implementations actions 1062, 1064, and 1066, may be performed in an automated process from which human participation may be omitted.

Thus, the present application discloses systems and methods for performing ML model based condition and property detection. In the exemplary use case of infectious disease prediction, the present ML model based diagnostic solution can render real-time disease state predictions for asymptomatic as well as symptomatic disease carriers in a manner that does not require special equipment or specially trained personnel, can be deployed rapidly, ubiquitously, and in a privacy-preserving way.

Moreover, the present application discloses a ML model based condition and property detection solution that can be deployed on any computer or smartphone either within its own application or embedded within another application. Consequently, the present ML model based condition and property detection solution can advantageously be deployed in an active manner, such as part of a multi-step screening process at a public or private event, or in any venue, such as an airport or cruise ship, for example, designed to host large groups. Alternatively the present ML model based condition and property detection solution may be deployed in an ambient manner (working in the background of a mobile phone software application for example) and thereby create a system that can not only provide notice to the individual user, but may also, when the user opts in or otherwise gives informed consent, contribute to national or global real-time status/outbreak warning systems. It is emphasized that even this use case can be implemented in a privacy preserving way, because, as noted above, this ML model based condition and property detection solution can be deployed locally on each device, not requiring the sending of audio data or PII to an external server in order to render a disease state or other prediction. Additionally, because the present ML model based condition and property detection solution can employ a multi-step automated segmentation process, as described above, which allows for unstructured input data to be usable for both training and prediction purposes, it advantageously produces normalized datasets that are ideally suited for machine learning.

From the above description it is manifest that various techniques can be used for implementing the concepts described in the present application without departing from the scope of those concepts. Moreover, while the concepts have been described with specific reference to certain implementations, a person of ordinary skill in the art would recognize that changes can be made in form and detail without departing from the scope of those concepts. As such, the described implementations are to be considered in all respects as illustrative and not restrictive. It should also be understood that the present application is not limited to the particular implementations described herein, but many rearrangements, modifications, and substitutions are possible without departing from the scope of the present disclosure.

What is claimed is:

1. A system comprising:

a computing platform including a processing hardware and a system memory;

a software code including a trained machine learning (ML) model stored in the system memory, the trained ML model including: (i) an input stage created based on a first ML model trained to detect one or more predetermined data attributes, the input stage trained using sliding window convolutions with stride length being a tunable hyperparameter of the input stage and a training dataset generated by a second ML model trained using an output of the first ML model and that has been annotated to identify the one or more predetermined data attributes, to predict bounding timestamps and to detect temporal segments of a test dataset that include the predetermined one or more data attributes, and (ii) an output stage trained using another training dataset that has been annotated to correlate the one or more predetermined data attributes with one of a condition or a property;

the processing hardware configured to execute the software code to:

receive a dataset;

perform an analysis of the dataset, using the input stage of the trained ML model, to detect a presence of at least one predetermined data attribute, the at least one predetermined data attribute comprising an audio attribute including a voiced bilabial nasal sound or audio content corresponding to operation of a machine, wherein performing the analysis comprises automatically segmenting the dataset by identifying one or more temporal segments that include the at least one predetermined data attribute and extracting the one or more temporal segments based on bounding timestamps predicted by the input stage; and:

(a) predict, by applying the output stage to the extracted one or more temporal segments when the analysis of the dataset detects the audio attribute including the voiced bilabial nasal sound, a probability that the at least one predetermined data attribute is indicative of a respiratory condition or an infectious disease status of a human subject, or (b) predict, by applying the output stage to the extracted one or more temporal segments when the analysis of the dataset detects the audio attribute including the audio content corresponding to the operation of the machine, a probability that the at least one predetermined data attribute is indicative of a malfunction by the machine.

2. The system of claim 1, wherein the at least one predetermined data attribute further comprises a visual attribute of the dataset.

3. The system of claim 1, wherein the dataset includes or is derived from time-based audio.

4. The system of claim 1:

wherein predicting, using the output stage of the trained ML model, predicts whether at least one of the one or more temporal segments including the at least one predetermined data attribute is indicative of the respiratory condition or the infectious disease status of the human subject, or the malfunction by the machine.

5. The system of claim 1, wherein the ML model is validated using a validation data having a known ground truth, by delivering the validation data as an input to the input stage and obtaining a prediction for the respiratory condition or the infectious disease status of the human subject, or a prediction for the malfunction by the machine as an output from the output stage.

6. The system of claim 1, wherein at least one of the input stage or the output stage of the trained ML model is trained using a federated learning process.

7. A method for use by a system including a computing platform having a processing hardware and a system memory storing a software code including a trained machine learning (ML) model including: (i) an input stage created based on a first ML model trained to detect one or more predetermined data attributes, the input stage trained using sliding window convolutions with stride length being a tunable hyperparameter of the input stage and a training dataset generated by a second ML model trained using an output of the first ML model and that has been annotated to identify the one or more predetermined data attributes, to predict bounding timestamps and to detect temporal segments of a test dataset that include the predetermined one or more data attributes, and (ii) an output stage trained using another training dataset that has been annotated to correlate the one or more predetermined data attributes with one of a condition or a property, the method comprising:

receiving, by the software code executed by the processing hardware, a dataset;

performing an analysis of the dataset, by the software code executed by the processing hardware and using the input stage of the trained ML model, to detect a presence of at least one predetermined data attribute, the at least one-predetermined data attribute comprising an audio attribute including a voiced bilabial nasal sound or audio content corresponding to operation of a machine, wherein performing the analysis comprises automatically segmenting the dataset by identifying one or more temporal segments that include the at least one predetermined data attribute and extracting the one or more temporal segments based on bounding timestamps predicted by the input stage; and:

(a) predicting, by the software code executed by the processing hardware using the output stage applied to the extracted one or more temporal segments when the analysis of the dataset detects the audio attribute including the voiced bilabial nasal sound, a probability that the at least one predetermined data attribute is indicative of a respiratory condition or an infectious disease status of a human subject, or (b) predicting, by the software code executed by the processing hardware using the output stage applied to the extracted one or more temporal segments when the analysis of the dataset detects the audio attribute including the audio content corresponding to the operation of the machine, a probability that the at least one predetermined data attribute is indicative of a malfunction by the machine.

8. The method of claim 7, wherein the at least one predetermined data attribute further comprises a visual attribute of the dataset.

9. The method of claim 7, wherein the dataset includes or is derived from time-based audio.

10. The method of claim 7:

wherein predicting, using the output stage of the trained ML model, predicts whether at least one of the one or more temporal segments including the at least one predetermined data attribute is indicative of the respiratory condition or the infectious disease status of the human subject, or the malfunction by the machine.

11. The method of claim 7, wherein training of the trained ML model further comprises:

validating the ML model, by the software code executed by the processing hardware and using a validation data having a known ground truth, by delivering the validation data as an input to the input stage and obtaining a prediction for the respiratory condition or the infectious disease status of the human subject, or a prediction for the malfunction by the machine as an output from the output stage.

12. The method of claim 7, wherein at least one of the input stage or the output stage of the trained ML model is trained using a federated learning process.

* * * * *